United States Patent [19]

Yukl

[11] Patent Number: 4,532,939
[45] Date of Patent: Aug. 6, 1985

[54] NONCONTACTING, HYPERTHERMIA METHOD AND APPARATUS FOR DESTROYING LIVING TISSUE IN VIVO

[76] Inventor: Tex Yukl, Pleasant Valley Rte., Box 21, Baker, Oreg. 97814

[21] Appl. No.: 434,823

[22] Filed: Oct. 18, 1982

[51] Int. Cl.³ ............................................. A61N 5/02
[52] U.S. Cl. .................................... 128/804; 128/736; 324/58.5 A; 374/122
[58] Field of Search ............. 128/804, 399, 736, 24 A; 374/122; 324/58.5 A

[56] References Cited

U.S. PATENT DOCUMENTS

| | | | |
|---|---|---|---|
| 4,234,844 | 11/1980 | Yukl | 324/58.5 A |
| 4,271,848 | 6/1981 | Turner et al. | 128/804 |
| 4,346,716 | 8/1982 | Carr | 128/804 X |
| 4,390,026 | 6/1983 | Christman | 128/804 X |
| 4,397,314 | 8/1983 | Vaguine | 128/804 X |

FOREIGN PATENT DOCUMENTS

| | | | |
|---|---|---|---|
| 2417263 | 10/1975 | Fed. Rep. of Germany | 128/804 |
| 2648908 | 5/1978 | Fed. Rep. of Germany | 128/804 |

Primary Examiner—Lee S. Cohen
Attorney, Agent, or Firm—Kolisch, Hartwell & Dickinson

[57] ABSTRACT

A noncontacting method and apparatus which uses heat to destroy tumor cells in living tissue. A bidirectionally focused beam of electromagnetic energy, having a pair of electrically and thermally related, spaced focal regions, is positioned so that one of its focal regions embraces a tumor site within living tissue and the other focal region embraces a simulated tumor which is disposed in a liquid medium contained in a tank. Thermal conditions occurring in the focal region embracing the simulated tumor are monitored to reflect thermal conditions occurring within the tumor site. Positioning of the beam is continued until preselected time and temperature conditions are attained which indicate that cell death has occurred within the tumor site.

5 Claims, 3 Drawing Figures

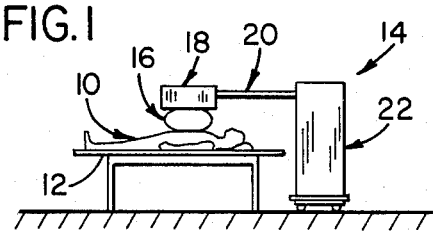
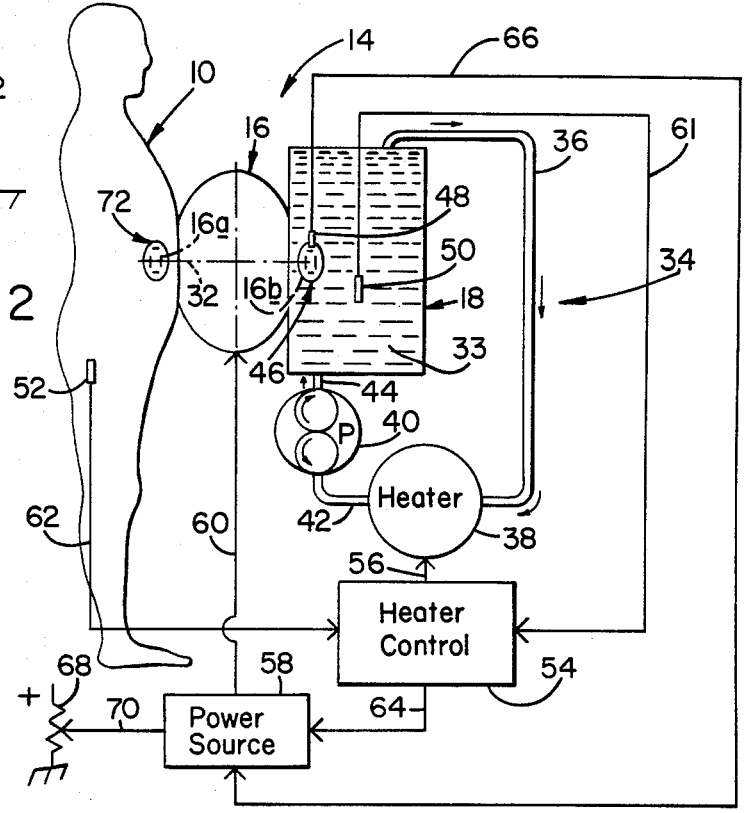
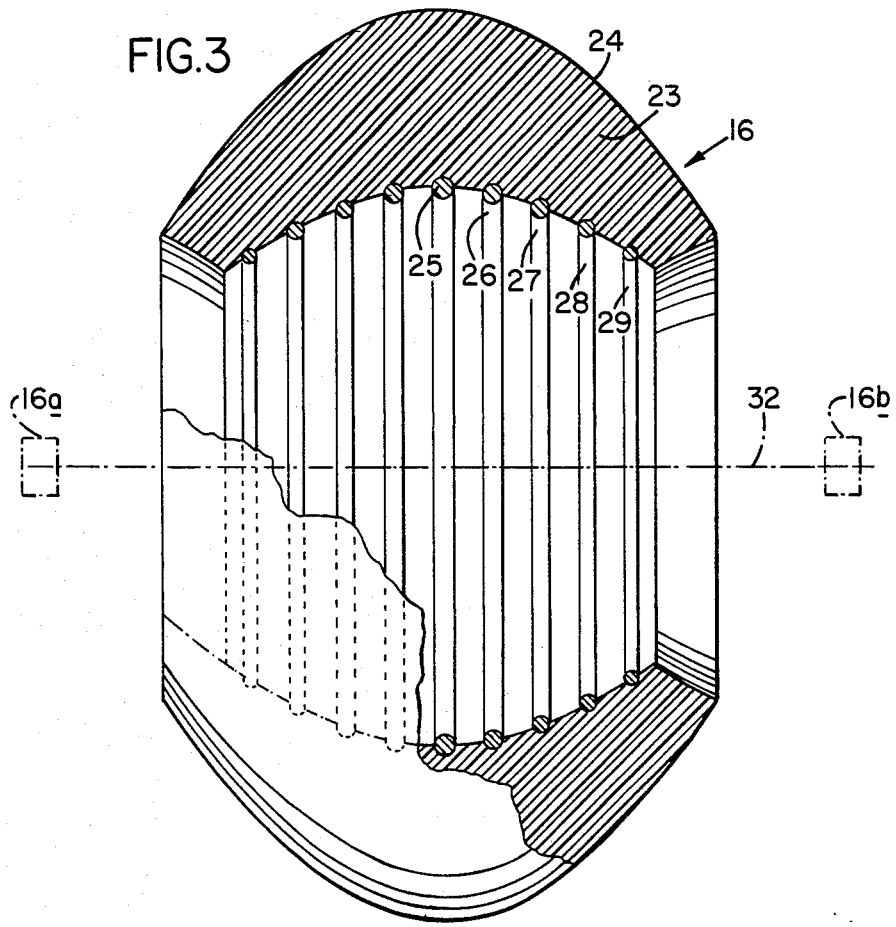

NONCONTACTING, HYPERTHERMIA METHOD AND APPARATUS FOR DESTROYING LIVING TISSUE IN VIVO

BACKGROUND AND SUMMARY OF THE INVENTION

This invention pertains to a method and apparatus for the hyperthermia destruction of tumors or the like. More particularly, it relates to such a method and apparatus which is noninvasive, and which employs bidirectionally radiated and focused electromagnetic energy generated by a special-purpose antenna constructed in accordance with the teachings of a prior U.S. patent of mine—identified below.

Current methods for the treatment of tumors in humans and animals include surgery, chemotherapy, and hyperthermia techniques such as X-ray irradiation, ultrasound, nuclear radiography, and electromagnetometry using convection. Numerous problems, however, are associated with all of these methods. For example, surgical removal of a tumor is highly invasive, and has all the attendant risks of any surgery, which are particularly enhanced with seriously ill patients. In addition, certain tumors are inoperable due to their position and formation in the body. Chemotherapy and hyperthermia techniques using X-ray irradiation, ultrasound, nuclear radiography, and electromagnetometry are all non-specific—generally exposing the entire body, and thereby generating a host of serious side effects.

A general object, therefore, of the present invention is to provide a unique, noncontacting, in vivo hyperthermia method and apparatus for destroying tumor cells and the like in a localized, circumscribed area, without destruction of surrounding tissue.

More specifically, an object of the invention is to provide such a method and apparatus that employs heat generated by an antenna which focuses and radiates two beams of electromagnetic energy bidirectionally so as to converge upon a pair of spaced focal regions, one of which embraces a tumor site inside a body, and the other which embraces a "simulated tumor" positioned outside the body.

Study of biological tissues indicates rather large differences in dielectric constants among various tissues. For example, skin and bone each has a dielectric constant of about [9], brain tissue a dielectric constant of about [34], muscle about [52], blood about [72], and cerebrospinal fluid a dielectric constant of about [80]. It is also established that tumor cells exhibit an approximate dielectric constant of [36], whereas normal cells surrounding tumors, which are typically fat cells, exhibit an approximate dielectric constant of [15].

As disclosed in my U.S. Pat. No. 4,234,844, issued Nov. 18, 1980, entitled "Electromagnetic Noncontacting Measuring Apparatus", it is possible to monitor such differing electrical parameters by generating and focusing electromagnetic energy at a pair of electrically related, spaced-apart focal points. According to the teachings of this patent, a bidirectional microwave antenna, made in accordance both with this patent, and with my companion U.S. Pat. No. 4,318,108, (issued Mar. 2, 1982, and entitled "Bidirectionally Focusing Antenna") may be aimed to place one of its focal points, or regions, adjacent a preselected interrogation site inside a body wherein certain electrical characteristics are to be observed. By using a receiver located adjacent the other focal point, or region, it is possible, by monitoring voltage, current and phase conditions at the receiver, to determine related electrical conditions at the interrogation site.

In the present invention, such an antenna is used to focus electromagnetic radiation bidirectionally toward a pair of spaced-apart focal regions that are disposed symmetrically with respect to the antenna. One of the focal regions is placed inside a patient's body to embrace a tumor site, while the other focal region is positioned to embrace an external simulated tumor having substantially the same dielectric constant as the "real" tumor. The simulated tumor is suspended in a tank containing a liquid medium with, as near as it is possible to attain, the same temperature and dielectric constant as the healthy tissue surrounding the real tumor. The temperature of the simulated tumor is then monitored to indicate the temperature of the "real" tumor. Once a preselected temperature, known to cause cell death, is reached at the simulated tumor, that temperature is maintained over a predetermined period of time until cell death within the "real" tumor site has occurred.

In the operation just described, destruction of a tumor is accomplished without physical invasion of the body. Further, due to localization of electromagnetic radiation, destruction of the tumor is accomplished without concomitant destruction of neighboring normal tissue having substantially lower dielectric constants than tumors—a condition important to proper application of this invention.

These and other objects and advantages which are attained by the invention will become more fully apparent as the description which now follows is read in conjunction with the accompanying drawings.

DESCRIPTION OF THE DRAWINGS

FIG. 1 is a highly simplified side elevation showing the apparatus of the invention in use with respect to a patient shown lying on a support table.

FIG. 2 shows, schematically, and in block form, and without regard to precise scale, details of the apparatus of FIG. 1.

FIG. 3 is a side elevation, partly in cross-section, illustrating an antenna which is used in the apparatus of FIGS. 1 and 2, with the antenna shown removed from all other associated structure.

DETAILED DESCRIPTION OF THE INVENTION

Referring first to FIG. 1, shown there in highly simplified form is a patient 10, lying on a table 12, receiving, according to the method of the invention, hyperthermia treatment from apparatus, shown generally at 14, which is constructed in accordance with the present invention. Generally speaking, apparatus 14 includes an antenna, or energy transmitter, 16 (positioned immediately above the chest of patient 10), mounted on the underside of a special container 18. Container 18 is supported on a positionally adjustable arm 20 which extends from a base, or mounting means, 22. Circuitry for powering antenna 16, and for obtaining and recording data derived during a treatment procedure, is carried by base 22. Preferably, the base is castor-mounted to accommodate movement of apparatus 14 conveniently over the floor when desired.

Digressing for a moment into a discussion regarding antenna 16, it is important, in order for one to understand how the antenna coacts with other elements in apparatus 14, to have a basic understanding of how the antenna, per se, is constructed and performs. Directing attention especially to FIG. 3, where the antenna is shown isolated from other structure in the apparatus, one should note that antenna 16, as mentioned earlier, is constructed in accordance with the teachings of my prior U.S. Pat. Nos. 4,234,844 and 4,318,108.

To begin with, antenna 16 has been designed with a characteristic operating impedance of 487-ohms—a value which substantially corresponds with the mean impedance of tissue in the human body. Secondly, antenna 16 has further been designed to operate in the microwave-radiation spectrum with an operating frequency of about 333-megahertz—a frequency which has been found to be quite effective in the hyperthermic treatment of tumors up to depths of around 6-cms. The dimensions of antenna 16 herein are somewhat larger than the corresponding dimensions of the antenna described in my two U.S. prior patents, owing to the facts that antenna 16 has been designed to operate at a different frequency and with a different characteristic impedance. In all other respects, the two antennae are identical, and a reading of my two prior patents fully teaches the manner of calculating the sizes and configurations of the various parts making up antenna 16. Thus, antenna 16 includes a somewhat donut-shaped polystyrene focusing lens 23, the outside of which is coated with a suitable thin-film conductive layer, such as silver layer 24. Carried inside the lens are a central driven ring 25, bracketed, so-to-speak, by plural director rings, such as those shown at 26, 27, 28, 29 on the right side of ring 25 in FIG. 3.

The transmission axis of antenna 16 is shown at 32. When the antenna is energized, it radiates electromagnetic energy bidirectionally simultaneously along axis 32, concentrating energy at a first pair of mirror-image-related focal points, or regions, shown generally at 16a, 16b. It is this bi-directional focusing feature of antenna 16 which specially adapts it for use in apparatus 14, and in conjunction with the novel method of this invention. More particularly, as will become clear from a reading of my two prior above-referred to U.S. Patents, if one knows the voltage, current and phase characteristics of energy supplied to the antenna, and measures corresponding characteristics occurring at either one of the antenna's two focal regions, information regarding electrical conditions existing at the other focal region is immediately available.

With antenna 16 having the characteristic impedance and operating frequency mentioned, each of focal regions 16a, 6b resides substantially 5-cms away from the corresponding "exit faces" of the antenna. This feature makes it possible to place and maneuver one of the focal regions, such as region 16a, inside the human body, for example, without there being any physical invasion (i.e., as by surgery) of the body.

Returning now to complete, in detail, discussion of the construction of apparatus 14, let us direct attention particularly to FIG. 2. In this figure, the combination of antenna 16 and container 18 has been rotated 90° clockwise relative to the positions of these structures in FIG. 1. This has been done simply for convenience in presenting other related structure in FIG. 2.

In FIG. 2, antenna 16 is mounted with its right exit face in the figure abutting the left side of the container in the figure. Any suitable mounting structure may be used for this purpose. With the antenna so mounted, focal regions 16a, 16b, are disposed as indicated, with focal region 16b residing within container 18.

Container 18 is formed of any suitable liquid-impervious material which is also transparent to radiation at the operating frequency of antenna 16. A material which has been found appropriate for this purpose is plexiglas.

According to an important feature of the invention, container 18 is filled with a liquid medium 33 having a dielectric constant which is substantially the same as that of normal, healthy, human fat tissue. As was mentioned earlier, this amount typically to a dielectric constant of about [15]. While different liquid media may be selected, one which has been found to function extremely satisfactorily is a mixture by volume including 10% water and 90% carbon tetrachloride.

For a reason which will be explained shortly, it is important that liquid in container 18 be recirculatable, and to this end there is provided a liquid recirculation system shown generally at 34. System 34 includes a discharge conduit 36 which connects between the upper end of container 18 and the right side of a liquid heater 38. Connecting the opposite side of heater 38 with a pump 40 is a feed conduit 42. Finally, connecting the discharge side of pump 40 with the underside of container 18 is a conduit 44.

According to another important feature of the invention, suitably disposed inside container 18 is a mass of material, shown at 46, which is intended, in size and in dielectric composition, to simulate a tumor site in a patient's body. In the illustration now being given, mass 46, which is also referred to herein as a site simulator, has a volume of about 4-cubic cms and a dielectric constant of about [36]—which is the same as the dielectric constant found to characterize most tumors. Simulator 46 is, importantly, positioned in container 18 in such a manner that it occupies space substantially corresponding to antenna focal region 16b. In apparatus 14, simulator 46 is formed of conventional carbon-impregnated cross-linked polystyrene.

Also provided according to the invention are various monitoring devices, or means, which are provided for following various temperatures. More specifically, a conventional temperature sensor 48 is provided for monitoring the temperature of simulator 46; another temperature sensor 50 is provided for monitoring the temperature of the liquid in container 18; and a third temperature sensor, in the form of a conventional rectal probe 52, is provided for monitoring the body temperature of a patient such as patient 10.

Completing a description of what is shown in FIG. 2, indicated generally at 54 is a heater control circuit associated via a conductive connection 56 with heater 38. Shown in block form at 58 is a power source circuit which operates, through a cable 60, to energize antenna 16. Output signals from sensor 50 and probe 52 are fed over conductors 61, 62, respectively, to control inputs in the heater control circuit, as shown. A conductor 64 extends between control circuit 54 and an enable/disable input associated with power source circuit 58.

A control signal from temperature sensor 48 communicates via a conductor 66 with a comparator input terminal in power source circuit 58. This signal, through the action of appropriate conventional circuitry in source 58, is compared with an adjustable bias voltage provided through a variable resistor 68 and a conductor 70 to another comparator input for the power source circuit.

In FIG. 2, apparatus 14 is shown in a condition set up to treat a tumor, shown at 72, which is located, as shown, several centimeters inside the chest of patient 10. Through conventional X-rays or other techniques, the size and location of tumor 72 are generally known, and the apparatus is placed relative to the patient in such a manner that antenna focal region 16a substantially occupies, or embraces, the same space as the tumor.

Describing now a typical treatment procedure, let us assume, that, at the beginning of the procedure, the body temperature of patient 10 is at the usual normal temperature of 37° C., with tumor 72 also initially at this temperature, and with an ambient air temperature of about 25° C. Control signals provided by temperature sensor 50 and by rectal probe 52 affect the heater control circuit in such a manner that it operates heater 38 in the liquid recirculation system to produce a matching temperature of 37° C. in the liquid in container 18. This arrangement is important in two respects. First, it maintains an actual simulation of a patient's body temperature in the liquid in container 18, and thus provides for maximum accuracy in measuring thermal effects taking place in the patient during treatment. Second, it provides a way of checking that the patient's normal body temperature is maintained and not dangerously elevated during a treatment procedure. In the event that temperature equilibrium, as just mentioned, does not exist, or in the event that the patient'body temperature rises above normal, power source 58 is automatically disabled from operating.

Because of the way in which antenna 16, as previously outlined, operates, with simulator 46 simulating as accurately as possible the size and dielectric constant of tumor 72, and with the liquid in container 18 simulating the temperature and dielectric constant of normal healthy tissue in patient 10, monitoring of the temperature of simulator 46 is substantially the same as directly monitoring the temperature of cells in tumor 72. Accordingly, it is possible by monitoring this temperature to know what is taking place thermally within the tumor.

Through previously applied conventional calibration techniques, variable resistor 68 is adjustable to apply a reference voltage on conductor 70 which is directly relatable to finally-desired cell temperature for destruction of cells in tumor 72. Experience has shown that such a temperature is achieved at about 44° C. Accordingly, resistor 68 is adjusted to apply a reference voltage associated with a 44° C. temperature.

At the start of the procedure, and because of the comparison which takes place, as previously suggested, in the power source circuitry between the reference voltage and a signal coming from temperature sensor 48, antenna 16 is energized with power at the level of about 200-watts (rms). This action immediately begins the process of heating both the cells in tumor 72, and the substance making up simulator 46. Practice has shown that with starting temperatures like those outlined above, this situation will remain for a period of around 15- to 25-minutes, with simulator 46, and hence tumor 72, at the end of this time having the desired 44° C. temperature. As the temperature of simulator 46 rises, the compared signals in the power source circuitry cause a gradual and continual lessening of the operating power for the antenna, with a final "maintenance" power level of around 5- to 20-watts (rms) existing when the 44° C. temperature has been achieved. This condition is then maintained for a period of about 45-minutes, at the end of which the cells in tumor 72 will have been destroyed. The apparatus then automatically shuts down.

It should thus be apparent how the apparatus of the invention, and the treatment method which it affords, amply meet all of the objects and advantages mentioned earlier. Among the striking advantages of this method and apparatus are that they require no surgical invasion of a patient's body, and that they can localize heat concentration precisely enough to destroy selected tumor tissue alone, without injuring surrounding healthy tissue. So long as all of the monitoring and operating features are performable as outlined above, the exact constructions of the liquid recirculation system, of the heater control circuitry, and of the power source circuitry are of no particular concern. In other words, various different designs may be used for these elements to suit different purposes.

Reviewing, therefore, the method proposed by the invention, three different views of this method are taken herein. According to one view, the method includes the following steps:

(1) Creating a pair of spaced electromagnetic-energy focal regions in which electrical, and therefore thermal, changes occurring adjacent one of the focal regions produce related electrical and thermal changes adjacent the other.

(2) Placing one of the focal regions inside tissue that is adjacent the location of the preselected site.

(3) Monitoring the electrical (thermal) conditions adjacent the location of the other focal region.

(4) Maintaining placement of the focal region inside the tissue until monitoring reflects that a predetermined electrical (thermal) condition has existed adjacent the other focal region over a predetermined period of time.

A second view of the method of the invention includes the following steps:

(1) Generating and radiating a beam of electromagnetic energy bidirectionally toward a pair of spaced focal regions in which an electrical, and therefore thermal, change occurring in one of the regions effects a related electrical and thermal change in the other focal region.

(2) Directing the beam in such a manner to place one of its focal regions inside a preselected site in living tissue.

(3) Monitoring electrical, thermal, conditions at the location of the other focal region.

(4) Finally, continuing to direct the beam until a predetermined temperature is maintained over a predetermined period of time in the other focal region, so as to cause cell destruction in the preselected site.

The third view includes the following steps:

(1) Generating and radiating a beam of electromagnetic energy bidirectionally toward a pair of spaced focal regions in which an electrical, and therefore thermal, change occuring in one effects a related electrical and thermal change in the other.

(2) Positioning the beam so as to place one of its focal regions within a preselected site in living tissue, and its other focal region within an external material having a dielectric constant substantially equal to the dielectric constant of the preselected site.

(3) Monitoring the electrical (thermal) conditions occurring in the material.

(4) Continuing the positioning of the beam until a predetermined temperature is maintained over a predetermined period of time in the material, thereby causing cell destruction within a preselected site.

Accordingly, while a preferred construction for, and method of practicing, the invention have been disclosed herein, it is appreciated that variations and modifications therein may take place without departing from the spirit of the invention.

It is claimed and desired to secure by Letters Patent:

1. A noninvasive, noncontacting method for causing cell destruction in a preselected site in living tissue through a technique employing an external tissue simulator, said method comprising creating a pair of spaced electromagnetic-energy focal regions wherein energy-effected electrical/thermal changes occurring adjacent one produce related electrical/thermal changes adjacent the other, placing one of such focal regions inside such tissue adjacent the location of such preselected site, placing the other focal region inside such external tissue simulator, monitoring the electrical/thermal conditions adjacent the location of the other focal region in such simulator, and maintaining the placement of such one focal region until said monitoring indicates that a predetermined electrical/thermal condition has existed in such simulator over a predetermined period of time.

2. A noninvasive, noncontacting method for causing cell destruction in a preselected site in living tissue through a technique employing an external tissue simulator, said method comprising generating a bidirectionally focused beam of electromagnetic energy, with such beam having a pair of spaced focal regions wherein an electrical, and therefore thermal, change occurring in one effects a related electrical/thermal change in the other, directing such beam so as to place one of its focal regions inside such tissue to embrace, at least partially, such preselected site, thus to place the other focal region inside such external tissue simulator, with the beam so directed, monitoring electrical/thermal conditions at the location of the other focal region in such simulator, and continuing so to direct the beam until a predetermined temperature is maintained over a predetermined period of time in such simulator, thus to cause cell destruction in such site.

3. A noninvasive, noncontacting method for causing cell destruction in a preselected site in living tissue through a technique employing an external tissue simulator, said method comprising generating a bidirectionally focused beam of electromagnetic energy, with such beam having a pair of spaced focal regions wherein an electrical, and therefore thermal, change occurring in one effects a related electrical/thermal change in the other, positioning such beam so as to place one of its focal regions within such tissue in a condition at least partially embracing the location of such preselected site, and its other focal region in a condition at least partially embracing the location of an external material having a dielectric constant substantially equal to the dielectric constant of such preselected site, monitoring the electrical/thermal conditons of the embraced portion of such material, and continuing said positioning until a predetermined temperature is maintained, over a predetermined period of time, within such embraced material portion, thus to cause cell destruction within the embraced portion of such preselected site.

4. Noncontacting, noninvasive hyperthermia apparatus for destrying cells at a preselected site in living tissue, where the cells is such site exhibit a dielectric constant within one known range, and the cells surrounding such site exhibit a dielectric constant within another known range, said apparatus comprising a container, a medium disposed in said container having a dielectric constant substantially equal to that of such surrounding cells, a site simulator supported within said medium having a dielectric constant substantially equal to that of the cells in such site, an energy transmitter capable, when energized, of creating related electrical/thermal conditions within positionally known spaced regions, means mounting said transmitter in a manner permitting simultaneous placement of said regions in positions with one at least partially embracing such preselected site and the other at least partially embracing said simulator, and means for monitoring changes in thermal conditions within said medium and within the embraced portion of said simulator.

5. The apparatus of claim 4, which further includes means for sensing the instantaneous temperature of the tissue cells surrounding such preselected site, and means operatively connected to said sensing means for establishing and maintaining in said medium a temperature which follows and substantially equals such instantaneous temperature.

* * * * *